US00PP08604P

United States Patent [19]

Kordes

[11] Patent Number: Plant 8,604

[45] Date of Patent: Feb. 22, 1994

[54] ROSE PLANT KORTENSES

[75] Inventor: Wilhelm Kordes, Sparrieshoop, Fed. Rep. of Germany

[73] Assignee: Bear Creek Gardens, Inc., Medford, Oreg.

[21] Appl. No.: 40,157

[22] Filed: Mar. 29, 1993

[51] Int. Cl.[5] ..... A01H 5/00

[52] U.S. Cl. ..... Plt./10

[58] Field of Search ..... Plt. 10

*Primary Examiner*—James R. Feyrer
*Assistant Examiner*—Bruce Campell
*Attorney, Agent, or Firm*—Klarquist, Sparkman, Campbell, Leigh and Whinston

[57] ABSTRACT

A miniature rose having bright, glossy green, disease-resistant foliage; bright red, semi-double flowers; ease of production using softwood cuttings; and vigorous, compact, well-branched habit of growth.

1 Drawing Sheet

The present invention relates to a new and distinct variety of rose plant of the miniature class which was originated by me by crossing an unnamed seedling with the variety Korlech.

This new variety evidences the following unique combination of characteristics which are outstanding in the new variety and which distinguish it from its parents, as well as from all other varieties of which I am aware:

1. Bright red, semi-double flowers borne in abundance;
2. Healthy, dark green, glossy foliage;
3. Vigorous, very compact habit of growth; and
4. Ease of propagation from softwood cuttings.

Asexual reproduction of this new variety by softwood cuttings, as performed at Wasco, Calif., and Sparrieshoop, Germany, shows that the foregoing characteristics and distinctions come true to form and are established and transmitted through succeeding propagations.

The accompanying illustration shows typical specimens of the vegetative growth and flowers of this new variety in different stages of development, depicted in color as nearly trus as it is reasonably possible to make the same in a color illustration of this character.

The following is a detailed description of my new rose cultivar with color descriptions using terminology in accordance with The Royal Horticultural Society (London) Colour Chart, except where ordinary dictionary significance of color is indicated.

Parentage:

*Seed parent.*—An unnamed seedling.

*Pollen parent.*—Korlech.

Classification:

*Botanical.*—Rosa hybrida.

*Commercial.*—Miniature.

FLOWER

Observations made from specimens grown in garden environments in Somis, Calif., and Sparrieshoop, Germany.

Blooming habit: Recurrent.

Bud:

*Size.*—½ inch when the petals start to unfurl.

*Form.*—Short, pointed ovoid.

*Color.*—When sepals first divide, bud color is Red Group 43A. When half blown, the upper and lower sides of the petals are Red Group 43A.

*Sepals.*—Color: Green Group 138A. Surface texture: Covered in fine hairs. There are three lightly appendaged sepals. There are two unappendaged sepals with hairy edges.

*Receptacle.*—Color: Green Group 143B. Shape: Funnel. Size: Small (⅛×⅛ inch). Surface: Smooth.

*Peduncle.*—Length: Short (1–1½ inches). Surface: Glandular. Color: Light green and bronzy. Strength: Stiff, erect, slender.

Bloom:

*Size.*—Small. Average open size is 1–1½ inches.

*Borne.*—Singly, and several together, in clusters. If in clusters: Flat.

*Stems.*—Short (4–6 inches).

*Form.*—When first open: Cupped. Permanence: Flattens, outer petal edges curl slightly.

*Petalage.*—Number of petals under normal conditions: 15–20.

*Color.*—The upper and reverse sides of the petals are Red Group 43A. The base of each petal has a yellow half moon (⅛×⅛ inch) at the point of attachment. The major color on the upper side is Red Group 43A.

*Variegations.*—None.

*Discoloration.*—No change in the general tonality at the end of the first day or at the end of the third day.

*Fragrance.*—Slight.

Petals:

*Texture.*—Thick.

*Shape.*—Round.

*Form.*—Tips slightly recurved.

*Arrangement.*—Imbricated, with few petaloids in the center.

*Persistence.*—Drop off cleanly.

*Lastingness.*—On the plant: Short (4–5 days). As a cut flower: Short (5 days).

Reproductive parts:

*Anthers.*—Size: Small. Quantity: Many. Color: Reddish brown. Arrangement: Regular around styles.

*Filaments.*—Color: Reddish brown.

*Pollen.*—Color: Gold yellow.

*Styles.*—Color: Red.

*Stigmas.*—Color: Greenish white.

Form: Bush.

Growth: Vigorous, dwarf, upright, branching, compact.

Foliage: Number of leaflets on normal mid-stem leaves: 5 or 7.

*Size.*—Small ($2\frac{1}{2} \times 1\frac{1}{2}$ inches).

*Quantity.*—Abundant.

*Color.*—New foliage: Reddish. Old foliage: Dark green.

Leaflets:

*Shape.*—Pointed oval.

*Texture.*—Upper side: Leathery, glossy.

*Edge.*—Serrated.

*Serration.*—Single, small.

*Petiole rachis.*—Color: Reddish green.

*Petiole underside.*—Smooth.

*Stipules.*—Medium, bearded.

*Disease resistance.*—Resistant to mildew and rust under normal growing conditions at Somis, Calif.

Wood:

*New wood.*—Color: Light green. Bark: Smooth.

*Old wood.*—Color: Green. Bark: Smooth.

Prickles:

*Quantity.*—On main canes from base: Ordinary. On laterals from main canes: Ordinary.

*Form.*—Short ($\frac{1}{8}$ inch), hooked downward.

*Color when young.*—Red.

Small prickles:

*Quantity.*—On main stalks: None. On laterals: None.

I claim:

1. A new and distinct variety of rose plant of the miniature class, substantially as herein shown and described, characterized particularly as to novelty by the unique combination of its bright, glossy green, disease-resistant foliage; bright red, semi-double flowers; ease of production using softwood cuttings; and vigorous, compact, well-branched habit of growth.

* * * * *

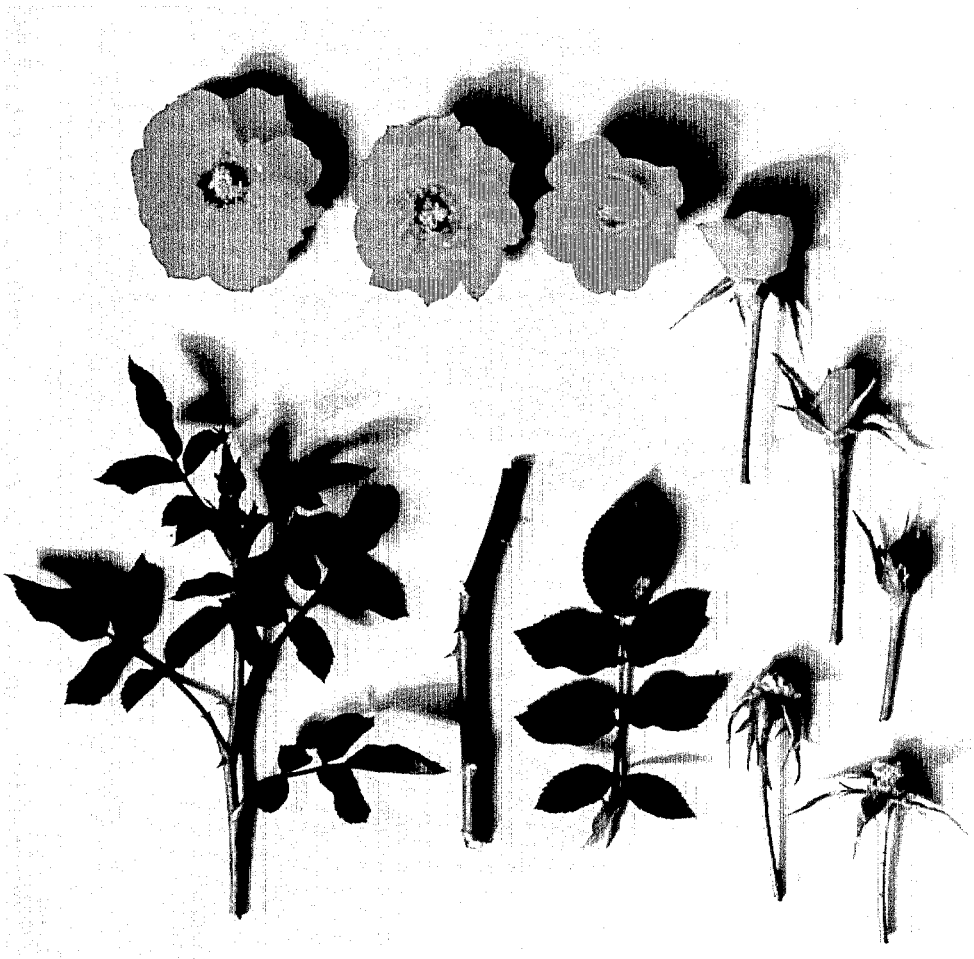
KOR tenses